United States Patent [19]
Kasahara

[11] Patent Number: 5,437,616
[45] Date of Patent: Aug. 1, 1995

[54] VALGUS BIG TOE RECTIFYING SUPPORTER

[76] Inventor: Iwao Kasahara, 3734-6, Totsukacho, Totsuka-ku, Yokohama-shi, Kanagawa, Japan

[21] Appl. No.: 65,825

[22] Filed: May 21, 1993

[30] Foreign Application Priority Data

Jun. 5, 1992 [JP] Japan .............................. 4-045236 U
Jul. 28, 1992 [JP] Japan .............................. 4-058348 U
Jul. 28, 1992 [JP] Japan .............................. 4-058349 U

[51] Int. Cl.⁶ ........................................... A61F 5/00
[52] U.S. Cl. ................................. 602/30; 128/894
[58] Field of Search ............................. 602/30, 5; 128/892–894, 882

[56] References Cited

U.S. PATENT DOCUMENTS

| | | |
|---|---|---|
| 1,103,465 | 7/1914 | Arrowsmith . |
| 1,497,151 | 6/1924 | Malkin . |
| 1,785,185 | 12/1930 | Day . |
| 2,190,016 | 2/1940 | Day et al. . |
| 2,332,473 | 10/1943 | Salander . |
| 2,416,823 | 3/1947 | Day . |
| 2,596,038 | 5/1952 | Mayer . |
| 3,049,120 | 8/1962 | Marcus . |
| 4,632,103 | 12/1986 | Fabricant et al. . |
| 4,637,381 | 1/1987 | Jungmann . |
| 4,644,940 | 2/1987 | Nakamura . |

*Primary Examiner*—Linda C. M. Dvorak
*Attorney, Agent, or Firm*—Jordan and Hamburg

[57] ABSTRACT

The present application is directed to a valgus big toe rectifying supporter which can prevent pain in and around a valgus big toe and its nail which will be caused by pressure exerted by the valgus toe or its nail, comprising a metatarsal joint securing band which will be firmly wound around the metatarsal joint at the root of the big toe laterally of the foot so that the metatarsal joint may be kept fastened, with this band turned upward, projection pieces extended from the upper end lower edge by the band, and a resilient body positioned between said projection pieces which will be inserted between the big toe and the second toe. The big toe can extend outward, so that its nail is not pressed to cause pain around it. Since the valgus big toe rectifying supporter can fit any big toe regardless of the thickness or length thereof, one can freely move the big toe thereby allowing easy walking.

11 Claims, 12 Drawing Sheets

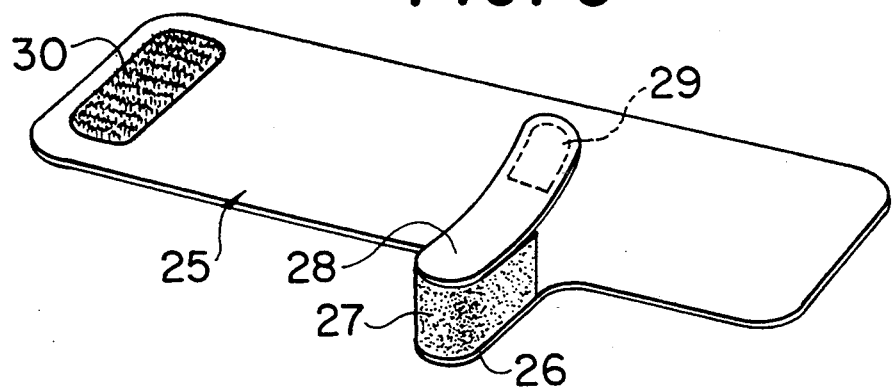
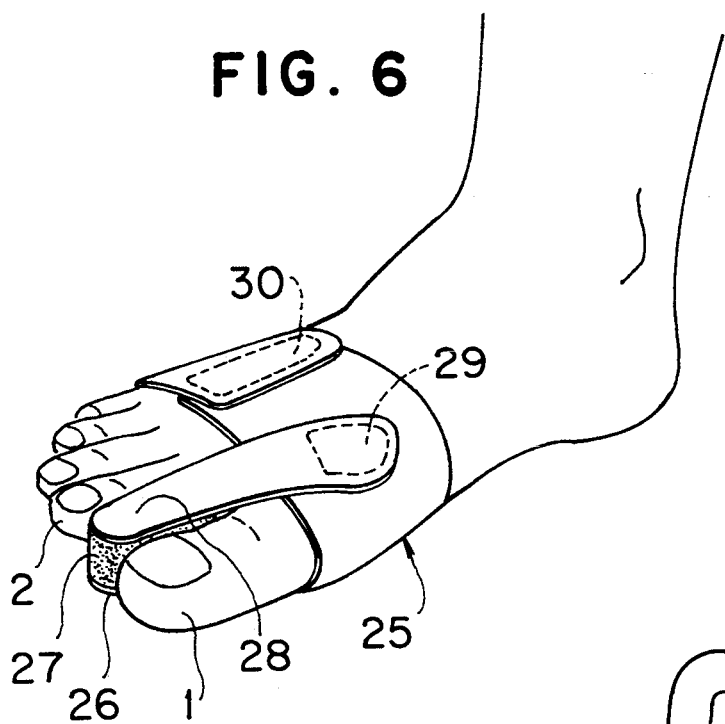
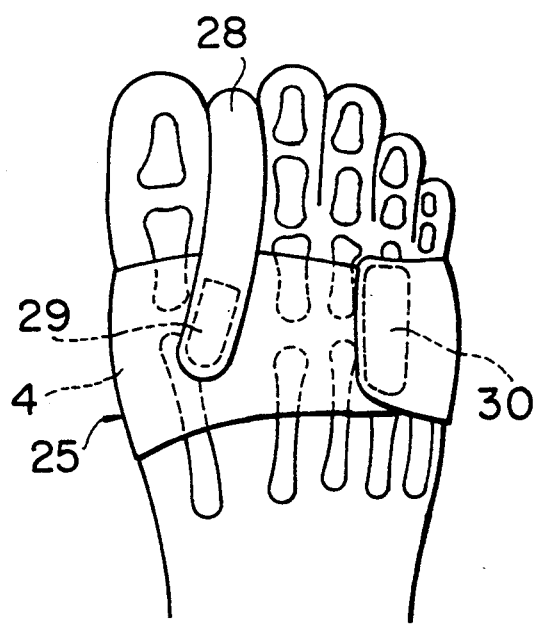

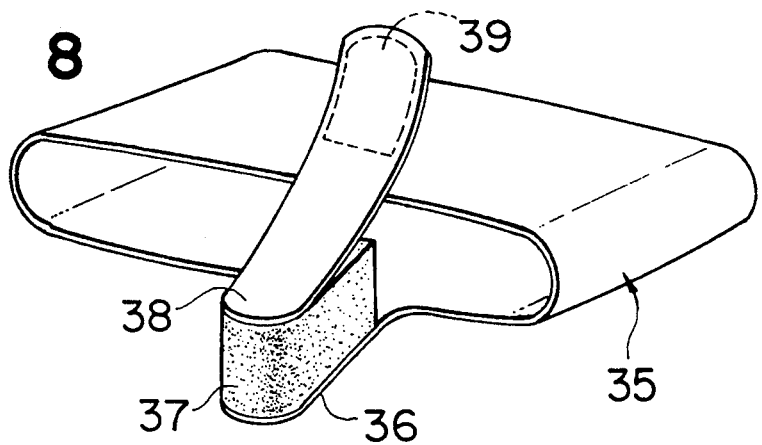
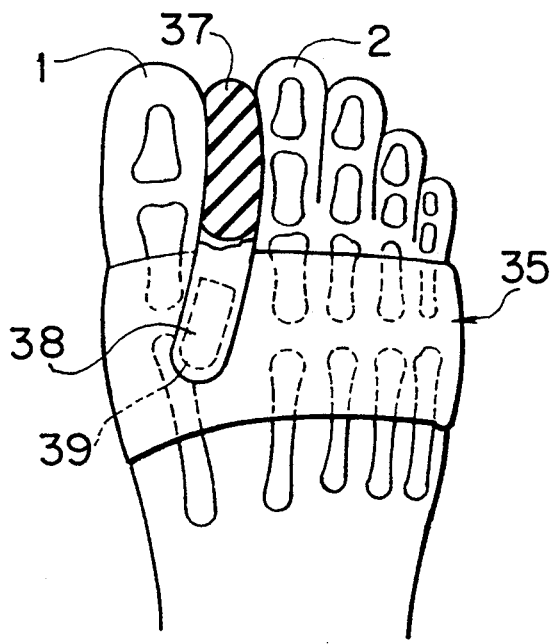
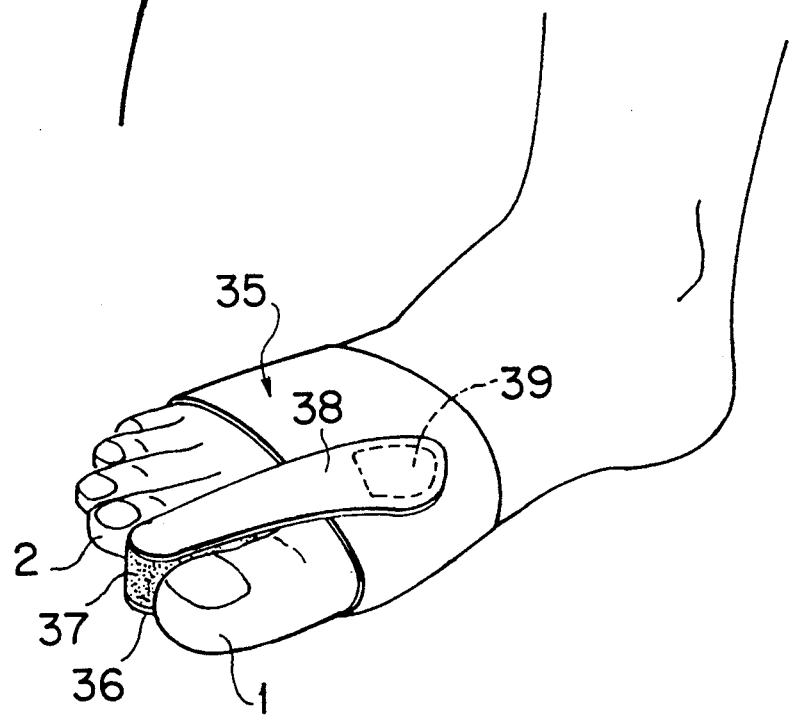

VALGUS BIG TOE RECTIFYING SUPPORTER

FIELD OF THE INVENTION

The present invention relates to a supporter for rectifying a valgus big toe. More particularly, the present invention relates to a valgus big toe rectifying supporter for rectifying a valgus big toe which has been bent toward the second toe back to its normal state.

PRIOR ART

As shown in FIG. 28, a valgus big toe is a deformed big toe 1 bent toward the second toe 2. This is caused when the transverse metatarsal band 3 has slackened, and particularly when the first metatarsal joint 4 has spread to cause the first toe 1 to be bent toward the second toe 2. The major cause which makes the big toe valgus is the fact that, these days, people seldom walk on the rugged ground and wear from their infant days shoes wherein they need not move their big toes, so that the toes are fixed. In particular, the toes are not required to move, thus lose the strength and gradually degenerate, so that it is considered that when one starts to run abruptly, the big toe is pushed outward and bent. It is said that other cause is attributed to the fact that since people wear shoes with narrow toes, they are liable to hurt the tips of their toes, the toes are tightened, and the big toes are bent outward.

When the big toe is tightened and bent outward in this way, not only one feels pain on the inside of the first metatarsal joint 4 at the root of the big toe 1, but also the walking strength becomes weak, the balance of the parallel legs becomes unstable, and one is apt to fall and get hurt.

To rectify the valgus big toe, the applicant suggested a valgus big toe rectifying supporter in Japanese Patent Application Publication No. 12094/1990 published on Mar. 19, 1990. The constitution of the valgus big toe rectifying supporter disclosed therein will now be described with reference to FIGS. 29 and 30. Reference numeral 11 indicates a cloth joint securing band for wrapping the first metatarsophalangeal joint together with other four metatarsophalangeal joints so that the first metatarsophalangeal joint section at the root of the big toe may be secured to its normal position. A hook and loop fastener is attached to almost all the outer surface of the joint securing band. Reference numeral 12 indicates a cloth big toe enclosing section connected to the joint securing band 11 which is capable of enclosing the big toe. Reference numeral 13 is a cloth pulling band which has an end 13a fixed to the outer side surface of the big toe enclosing section 12 and has a length which can extend from the end 13a along one outer side surface of the foot, then around the heel, and along the other outer side surface of the foot to the joint securing band 11. Hook and loop fasteners are attached to the pulling band 13 and the joint securing band 11 at parts where the puling band 13 will abut on the joint securing band 11. When the valgus big toe rectifying supporter is applied, the big enclosing section is put on the big toe. The whole joints are wrapped in the joint securing band 11. The first metatarsal joint section at the root of the big toe is fastened so that the first metatarsal joint section may be in its normal position and a wrapping end 11a is fixed to the hook and loop fastener on the outer surface. Then, the pulling band 13 is pulled inward so that the valgus big toe may be returned back to its normal position, a section 13b is fixed by the joint securing band 11, the pulling band 13 is put around the heel 14, and the other end 13c is fixed to the joint securing band 11 at the most suitable position by the hook and loop fastener. However, although this valgus big toe rectifying supporter is effective for rectifying a valgus big toe, the valgus big toe rectifying supporter has a defect that even thought the valgus big toe is pulled inward to the inner normal position, the big toe and its nail cannot be prevented from being pressed and one feels pain caused around the big toe or its nail.

SUMMARY OF THE INVENTION

An object of the present invention is to provide a valgus big toe rectifying supporter which is effective for rectifying a valgus big toe and can prevent one from having pain in the valgus big toe or around its nail which will be caused by pressure on the valgus big toe or its nail.

The valgus big toe rectifying supporter according to the present invention comprises a metatarsophalangeal joint securing band which will be firmly wound around the metatarsal joint at the root of the big toe laterally of the foot so that the metatarsal joint may be kept fastened, a hook and loop fastener provided at one end of said metatarsophalangeal joint securing band, first and second projection pieces extending from the forward edge of said metatarsophalangeal joint securing band, and a resilient member that is fixed between said first projection piece and said second projection piece and will be inserted between the big toe and the second toe. Owing to this constitution, the pressing force of a valgus big toe against the second toe is absorbed and weakened by the resilient member, the pain in the big toe and around its nail can be alleviated, and the deformed big toe can be rectified to its normal position. Using this valgus big toe rectifying supporter, the big toe can extend outward, so that its nail is not pressed to cause pain around it. The valgus bid toe rectifying supporter can fit various big toes, such as a thick big toe and a long big toe, and allows the big toe to move freely, and therefore, for example, there is an effect that one can exert a force in the big toe to make the walking easy.

BRIEF DESCRIPTION OF THE DRAWINGS

FIG. 5 is a perspective view of a third embodiment of the present invention.

FIG. 6 is a perspective view of the third embodiment of the present invention which shows the state in use.

FIG. 7 is a top view of the third embodiment of the present invention.

FIG. 8 is a perspective view of a fourth embodiment of the present invention.

FIG. 9 is a perspective view of the fourth embodiment of the present invention which shows the state in use.

FIG. 10 is a top view of a fourth embodiment of the present invention.

DESCRIPTION OF THE PREFERRED EMBODIMENTS

Figure 1:
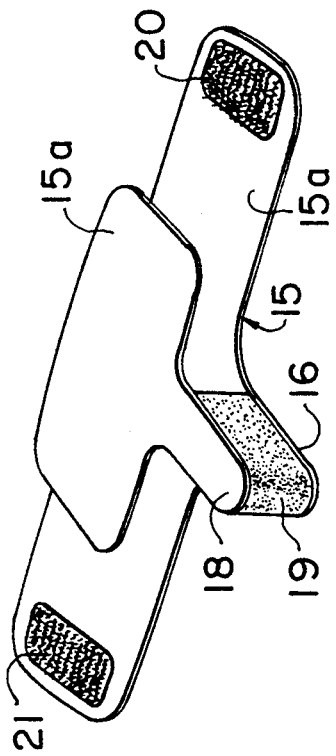
FIG. 1 is a perspective view of a first embodiment of the present invention.

A first embodiment of the present application will now be described with reference to FIGS. 1 and 2. A first-metatarsophalangeal joint securing band 5 is a felt band having a length to wrap laterally a section including the first metatarsophalangeal joint 4 of the big toe 1. A first projection piece 6 is extended from the front edge of a lower surface 5a between the big toe 1 and the second toe 2 and the band 5 is turned to form an insertion opening 7 so that the second toe, the third toe, the fourth toe, and the little toe can be inserted thereinto. Further, the band 5 has a second projection piece 8 extended from the front edge of an upper surface 5b and is opposed to the first projection piece 6 of the lower surface 5a and a resilient member 9 is fixed between the first and second projection pieces 6 and 8. The band upper surface 5b has its end extended slightly beyond the second projection piece 8 toward the big toe. The band lower surface 5a has a hook and loop fastener 10 fixed at its end section on the big toe side.

Figure 2:
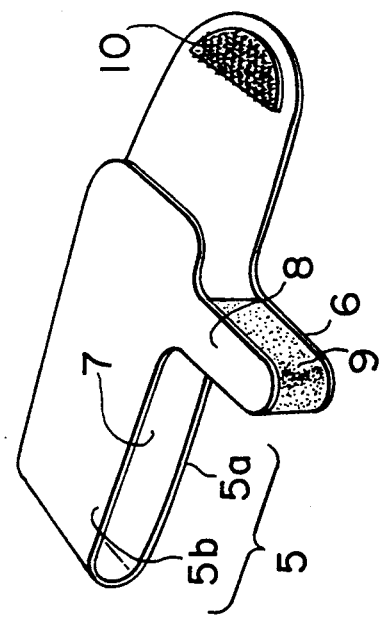
FIG. 2 is a perspective view of the first embodiment of the present invention which shows the state in use.
Figure 3:
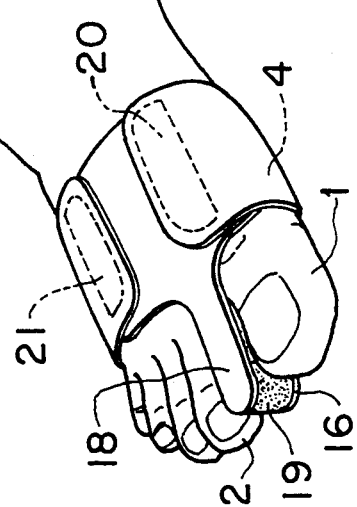
FIG. 3 is a perspective view of a second embodiment of the present invention.

When it is put to use, the second toe to the little toe are inserted into the insertion opening 7 shown in FIG. 1, the resilient member 9 is inserted between the big toe 1 and the second toe 2, one end of the band 5 is turned upward as shown in FIGS. 2 and 3, the section of the band 5 corresponding to the first metatarsophalangeal joint is pulled toward the little toe, and the hook and loop fastener 10 is attached fixedly to the end section of the upper surface 5b of the band 5 with the first metatarsophalangeal joint 4 fastened.

Now a second embodiment of the present invention will be described with reference to FIGS. 3 and 4. A lower section 15a of a first-metatarsophalangeal joint securing band 15 is the lower side section of the band of felt which will be wound laterally around a section including the first metatarsophalangeal joint 4 of the big toe 1 and reference numeral 15b indicates an upper side section. First and second projection pieces 16 and 18 are extended from the front edges between the bid toe 1 and the second toe 2 and a resilient member 19 is fixed between the projection pieces 16 and 18. Hook and loop fasteners 20 and 21 are fixed to both ends of the upper surfaces of the felt lower section.

Figure 4:
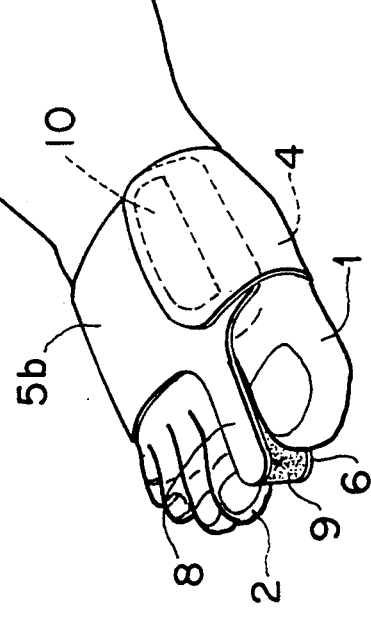
FIG. 4 is a perspective view of the second embodiment of the present invention which shows the state in use.

When it is put to use, as shown in FIG. 4, the resilient member 19 is inserted between the big toe 1 and the second toe 2, both the ends of the lower section of the band are turned upward, the section corresponding the first metatarsophalangeal joint 4 of the big toe 1 is pulled toward the little toe, and the hook and loop fasteners 20 and 21 are attached fixedly on the upper surface of the band upper section 15b with the first metatarsophalangeal joint 4 fastened.

A third embodiment of the invention will now be described with reference to FIGS. 5 to 7. The first-metatarsophalangeal joint securing band 25 is a felt band having a length to wrap laterally a section including the first metatarsophalangeal joins 4 of the big toe 1. A first projection piece 26 is extended from the front edge and a resilient member 27 is placed and fixed thereon. The forward end of a second projection piece 26 is fixed on the upper surface of the resilient member 27, the rear end is positioned on the upper surface of the band 25, a hook and loop fastener 29 is fixed to the undersurface thereof, and a hook and loop fastener 30 is attached fixedly on the upper surface of one end of the band 25. When it is put to use, as shown in FIGS. 8 to 10, the resilient member 27 is inserted between the big toe 1 and the second toe 2, the second projection piece 28 is raised, the section corresponding to the first metatarsophalangeal joint 4 of the big toe 1 is pulled by the band 25 toward the little toe, and the hook and loop fastener 30 is attached fixedly with the first metatarsophalangeal joint 4 fastened. Then, the second projection piece 28 is pulled toward the big toe 1 and while the big toe 1 is pressed toward its normal position the hook and loop fastener 29 is attached fixedly onto the band 25.

Now, a fourth embodiment of the present invention will be described with reference to FIGS. 8 to 10. A loop band 35 is resilient and has a circumference to wrap laterally a section including the first metatarsophalangeal joint 4 of the big toe 1. A first projection piece 36 is extended from the front edge between the big toe 1 and the second toe 2 and a resilient member 37 is placed and fixed on the first projection piece 36. The forward end of a second projection piece 38 is fixed on the upper surface of the resilient member 37, the rear end is positioned on the upper surface of the band 35, and a hook and loop fastener 30 is fixed to its undersurface.

When it is put to use, as shown in FIGS. 9 to 10, the band 35 is put on the particular foot with the resilient member 37 inserted between the first toe 1 and the second toe 2, the section corresponding to the first metatarsophalangeal joint 4 of the toe 1 is pressed toward the little toe, the second projection piece 38 is pulled toward the big toe 1 to push the big toe 1 to its normal position, and the hook and loop fastener 39 is attached fixedly on the band 35.

Figure 11:
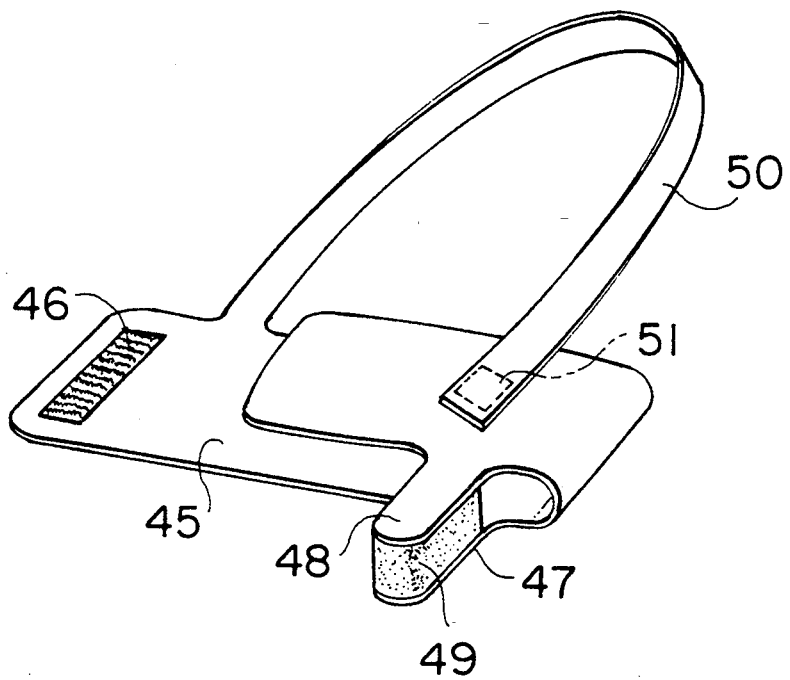
FIG. 11 is a perspective view of a fifth embodiment of the present invention.

A fifth embodiment of the present invention will now be described with reference to FIGS. 11 and 12. A first-metatarsophalangeal joint securing felt band 45 has a length to wrap laterally a section including first metatarsophalangeal joint 4 of the big toe 1 and a hook and loop fastener 46 is attached to an end thereof on the little toe side. First and second projection pieces 47 and 48 are extended from the lower and upper edges between the big toe 1 and the second toe and a resilient body 49 is fixed between the projection pieces 47 and 48. A pulling band 50 has a length capable of being put around the heel of the foot. One end of the pulling band 45 is integrally connected to the first-metatarsophalangeal joint securing band 45 on the little toe side and a hook and loop fastener 51 attached to the other end can be detachably attached on the upper surface of the first-metatarsophalangeal joint securing band 45 on the big toe side.

Figure 12:
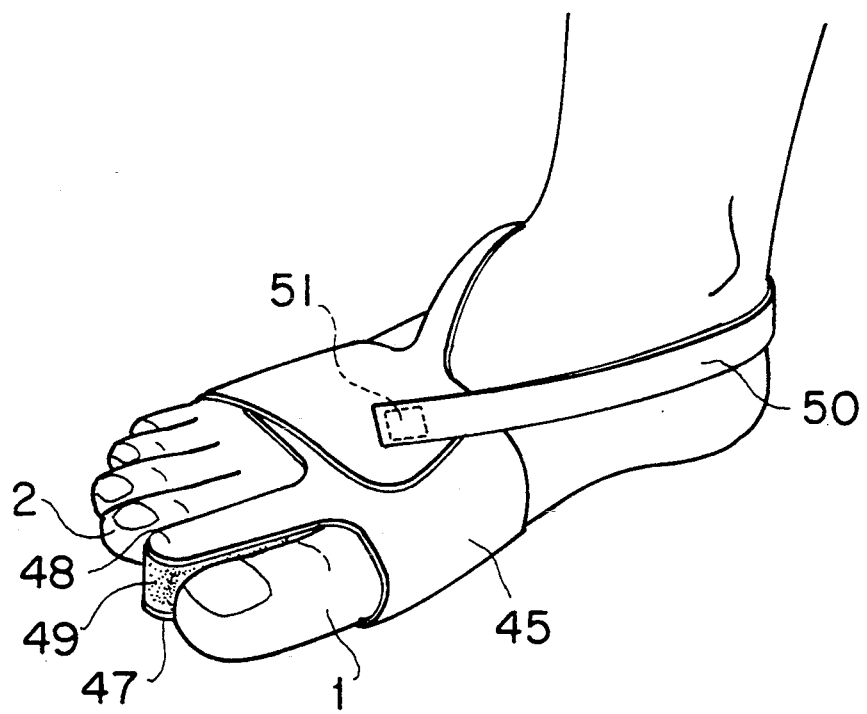
FIG. 12 is a perspective view of the fifth embodiment of the present invention which shows the state in use.

When it is put to use, as shown in FIG. 12, the resilient body 49 is inserted between the big toe 1 and the second toe 2, the first-metatarsophalangeal joint securing band 45 is fastened around the first metatarsophalangeal joint 4, the hook and loop fastener 46 is attached fixedly on the big toe side surface of the first-metatarsophalangeal joint securing band 45, the pulling band 50 is put around the heel of the foot, and the hook and loop fastener 51 is attached fixedly on the upper surface of the first-metatarsophalangeal joint securing band 45.

Figure 13:
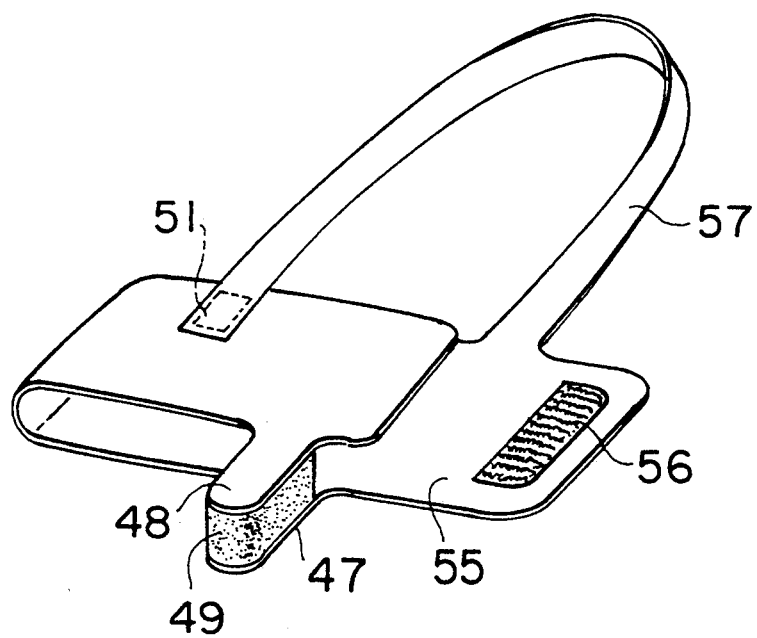
FIG. 13 is a perspective view of a sixth embodiment of the present invention.
Figure 14:
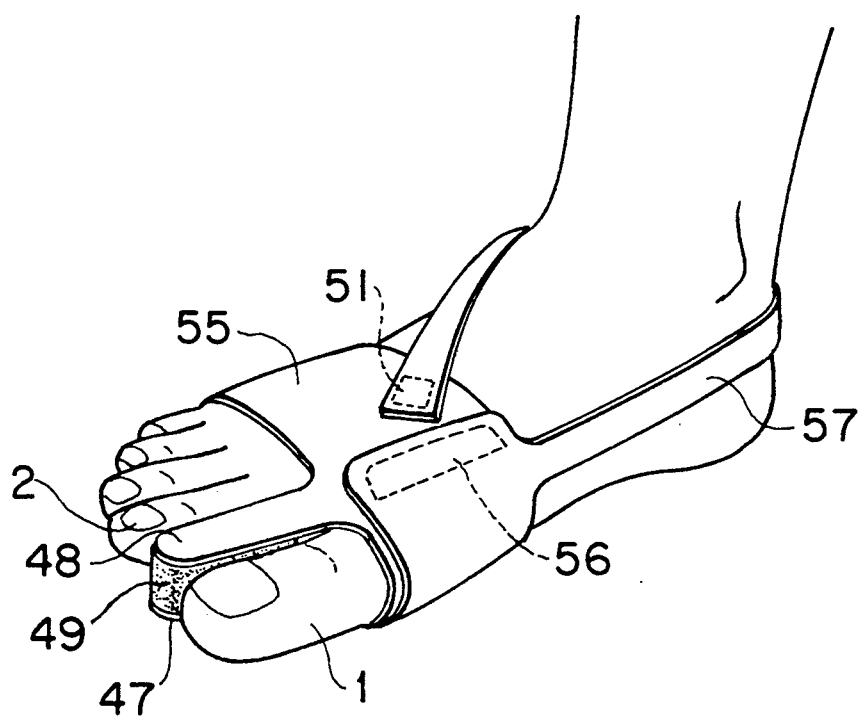
FIG. 14 is a perspective view of the sixth embodiment of the present invention which shows the state in use.

FIGS. 13 and 14 show a sixth embodiment of the present invention. A hook and loop fastener 56 is attached to a first-metatarsophalangeal joint securing band 55 on the big toe side, one end of a pulling band 57 that will be put around the heel of the foot is connected integrally to the big toe side of the first-metatarsophalangeal joint securing band 55, and a hook and loop fastener 56 attached to the other end is detachably attached on the little toe side upper surface of the first-metatarsophalangeal joint securing band 55. Since other structure are the same as those of the fifth embodiment, the same parts are indicated with the same reference numerals, and the description is omitted.

Figure 15:
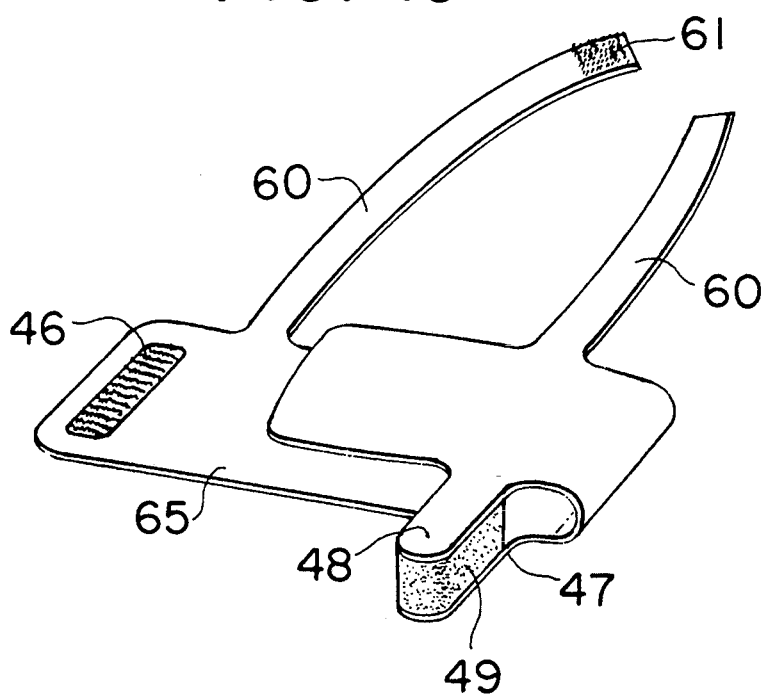
FIG. 15 is a perspective view of a seventh embodiment of the present invention.

FIG. 15 shows a seventh embodiment of the present invention. Both ends of a pulling band 60 are integrally connected to a first-metatarsophalangeal joint securing band 65, the middle section of the pulling band 60 is cut, hook and loop fasteners 61 are fixed to the cut ends of the pulling band 60, the pulling band 60 can be put around the ankle, and the hook and loop fasteners 61 can be joined together integrally. Since other structure is the same as that of the fifth embodiment, the same parts are indicated with the same reference numerals, and the description is omitted.

Figure 16:
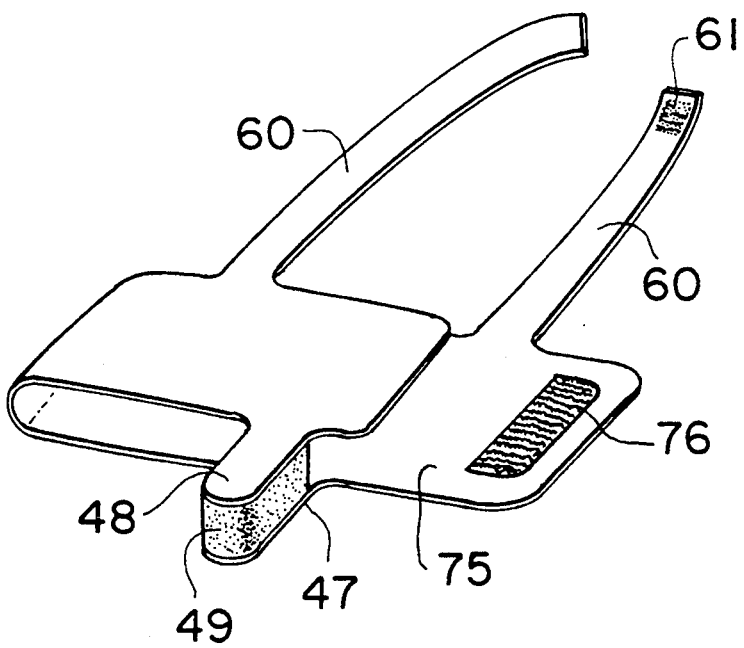
FIG. 16 is a perspective view of an eighth embodiment of the present invention.

FIG. 16 shows an eighth embodiment of the present invention, which is similar to the seventh embodiment, except that a hook and loop fastener 76 is attached to the little toe side of a first-metatarsophalangeal joint securing band 75, and since other structure is the same as that of the seventh embodiment, the same parts are indicated with the same reference numerals and the description is omitted.

Figure 17:
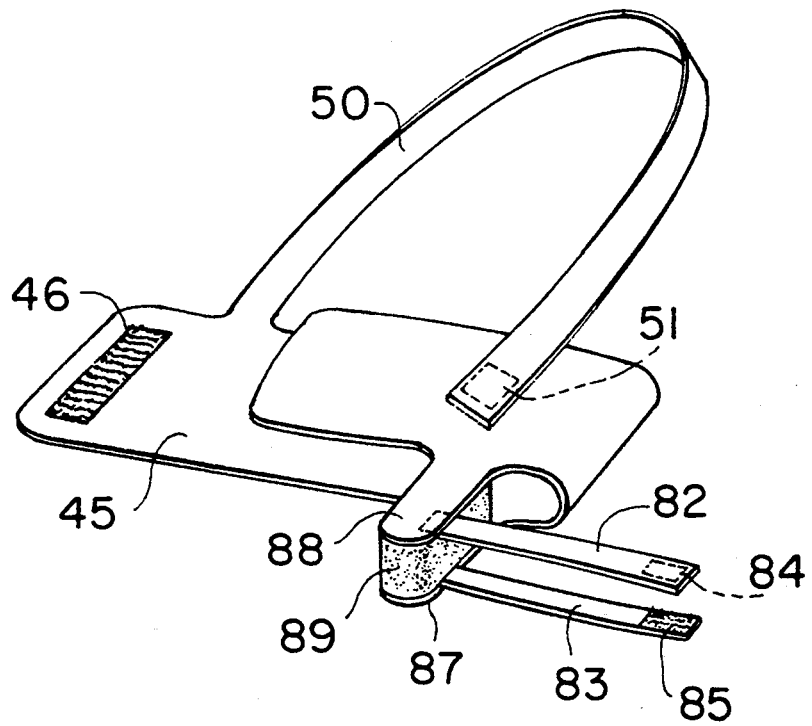
FIG. 17 is a perspective view of a ninth embodiment of the present invention.
Figure 18:
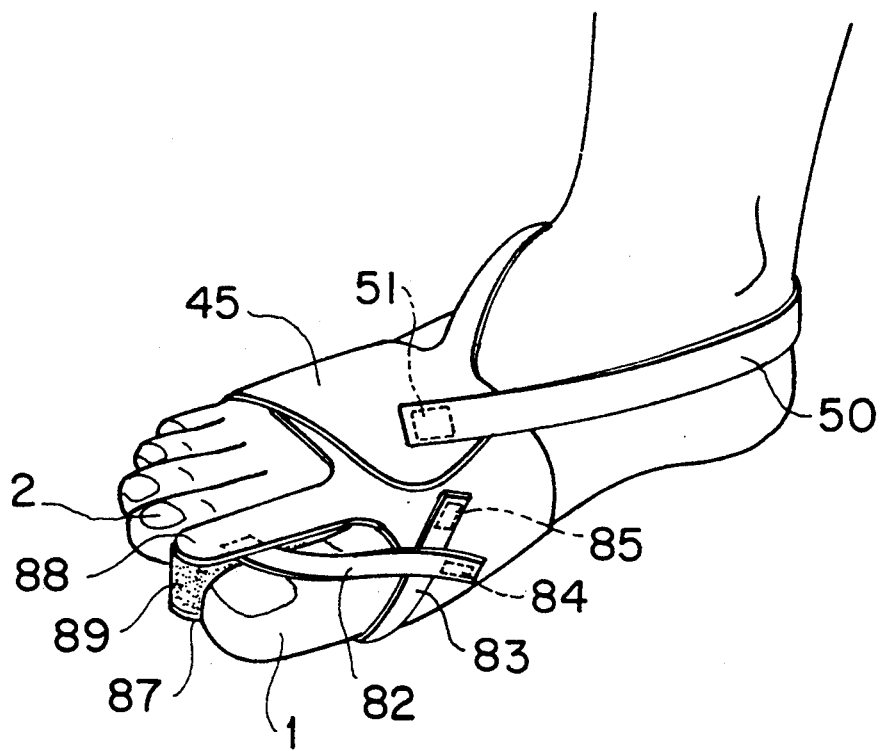
FIG. 18 a perspective view of the ninth embodiment of the present invention which shows the state in use.

FIGS. 17 and 18 show a ninth embodiment of the present invention. Big toe pulling bands 82 and 83 are extended outwardly of the big toe side from the forward ends of projection pieces 87 and 88 that support a resilient body 89, the bases of the big toe pulling bands 87 and 88 are fixed to the projection pieces 87 and 88, and the forward ends of the big toe pulling bands 87 and 88 have hook and loop fasteners 84 and 85 fixed thereto. Since other structure is the same as that of the embodiment shown in FIG. 5, the same parts are indicated with the same reference numerals and the description is omitted.

When it is put to use, as shown in FIG. 18, the resilient body 89 is inserted between the big toe 1 and the second toe 2, the metatarsophalangeal joint 4 is fastened with the metatarsophalangeal joint securing band 85, the hook and loop fastener 51 is attached fixedly on the upper surface of the big toe side of the first-metatarsophalangeal joint securing band 85, the pulling band 80 is put around the heel, and the hook and loop fastener 51 is attached fixedly on the surface of the first-metatarsophalangeal joint securing band 85. The big toe pulling bands 92 and 93 attached to the projection pieces 87 and 88 are crossed to allow the resilient body 89 to press the big toe 1 toward its normal state.

Figure 19:
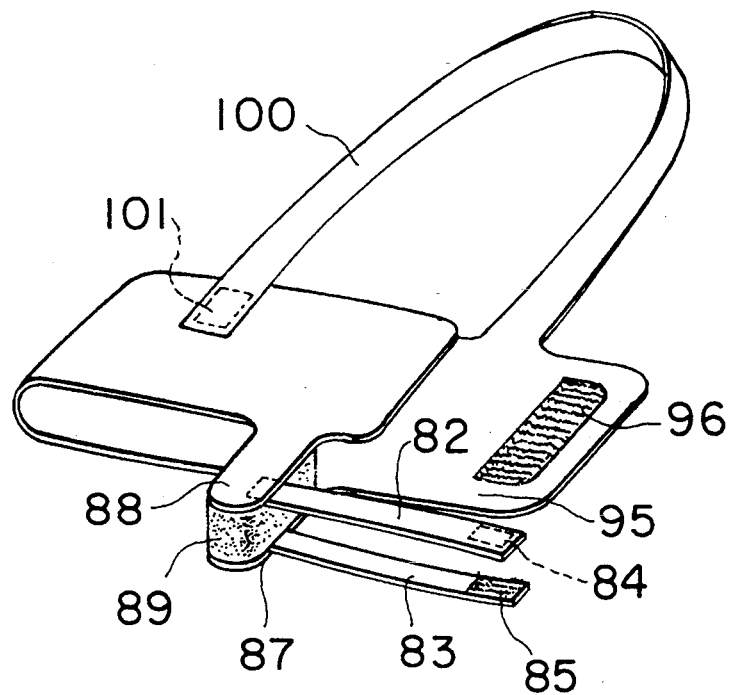
FIG. 19 a perspective view of a tenth embodiment of the present invention.
Figure 20:
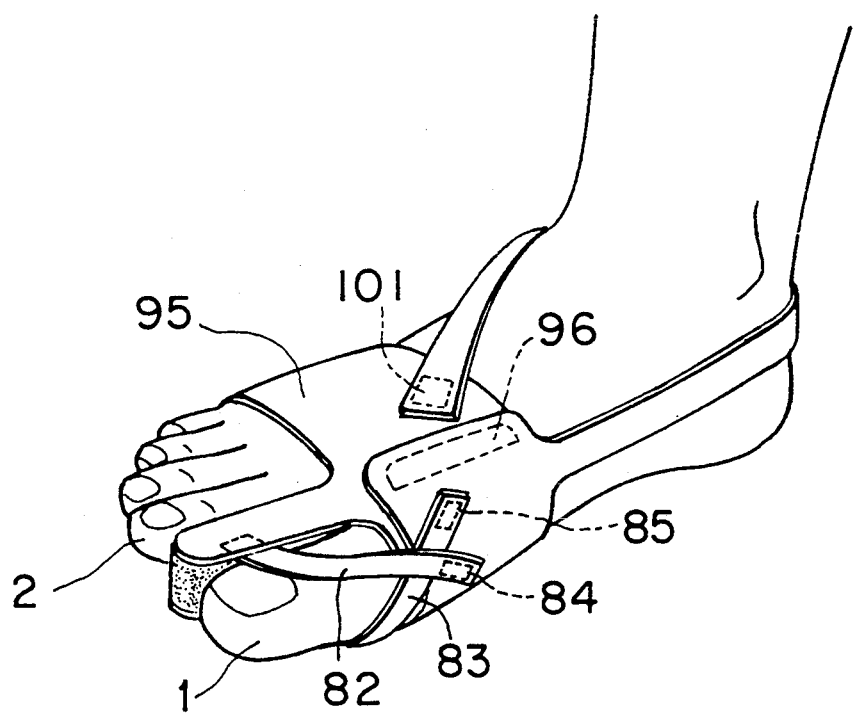
FIG. 20 is a perspective view of the tenth embodiment of the present invention.

FIGS. 19 and 20 show a tenth embodiment of the present invention. The tenth embodiment is similar to the ninth embodiment, except that the position of the velvet fastener 96 of the metatarsophalangeal joint securing band 95 and the position of the hook and loop fastener 101 of the pulling band 100 are changed to the opposite sides. Since other structure and function are the same as those of the ninth embodiment, the same parts are indicated with the same reference numerals and the description is omitted.

Figure 21:
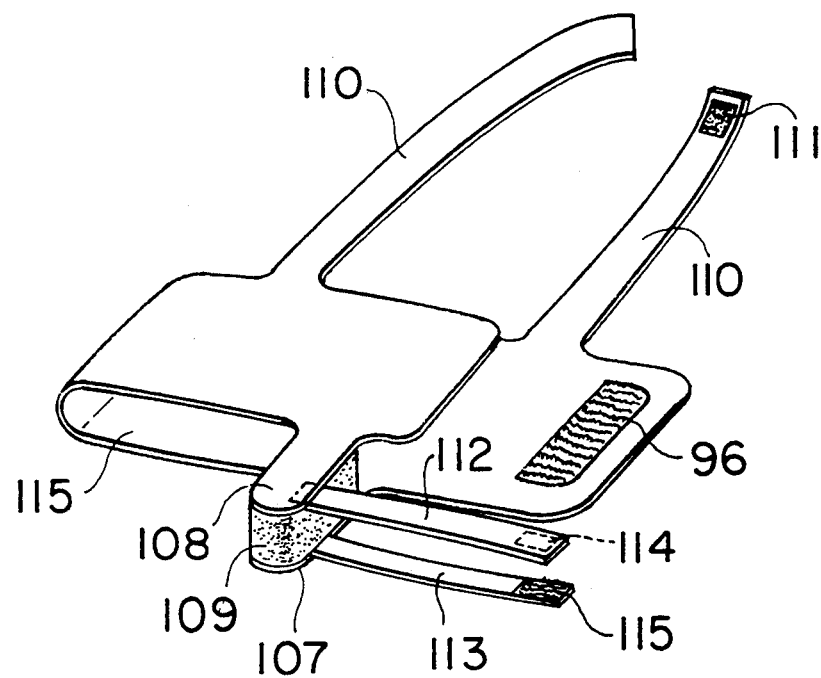
FIG. 21 is a perspective view of an eleventh embodiment of the present invention.
Figure 22:
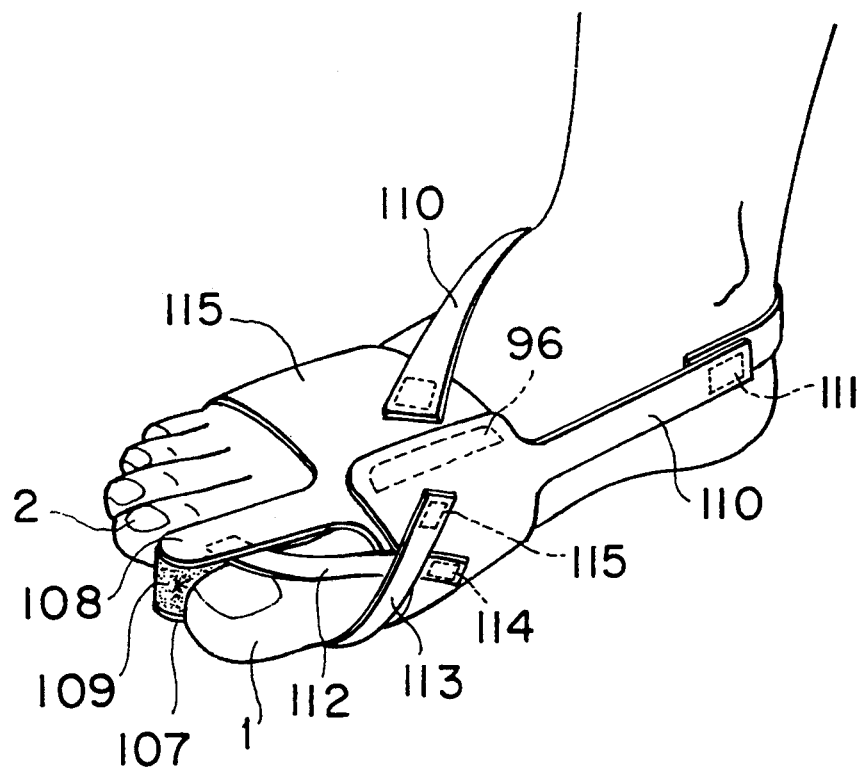
FIG. 22 shows a perspective view of the eleventh embodiment of the present invention which shows the state in use.

FIGS. 21 and 22 show an eleventh embodiment of the present invention. Big toe pulling bands 112 and 113 are arranged outwardly of the big toe side from the forward ends of first and second projection pieces 107 and 108 that support a resilient body 109 with the bases of the pulling bands 112 and 113 fixed to the projection pieces 107 and 108, and hook and loop fasteners 114 and 115 are fixed to the forward ends of the pulling bands 112 and 113.

When it is put to use, as shown in FIG. 22, the resilient body 109 is inserted between the big toe 1 and the second toe 2, a metatarsophalangeal joint securing band 115 was fastened to the metatarsophalangeal joint 4, the hook and loop fastener 114 is attached fixedly to the big toe side upper surface of the metatarsophalangeal joint securing band 115, the big toe pulling band 110 is put around the ankle, and the ends are connected by the hook and loop fasteners 111. Then, further, the big toe pulling bands 114 and 115 are crossed and pulled so that the big toe 1 may be pushed toward its normal position by the resilient body 109.

Figure 23:
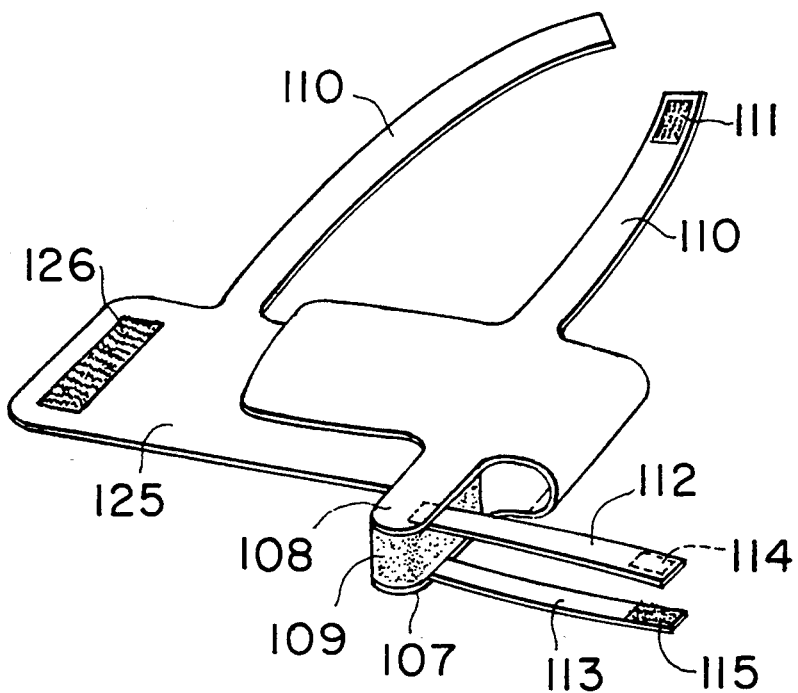
FIG. 23 is a perspective view of a twelfth embodiment of the present invention.
Figure 24:
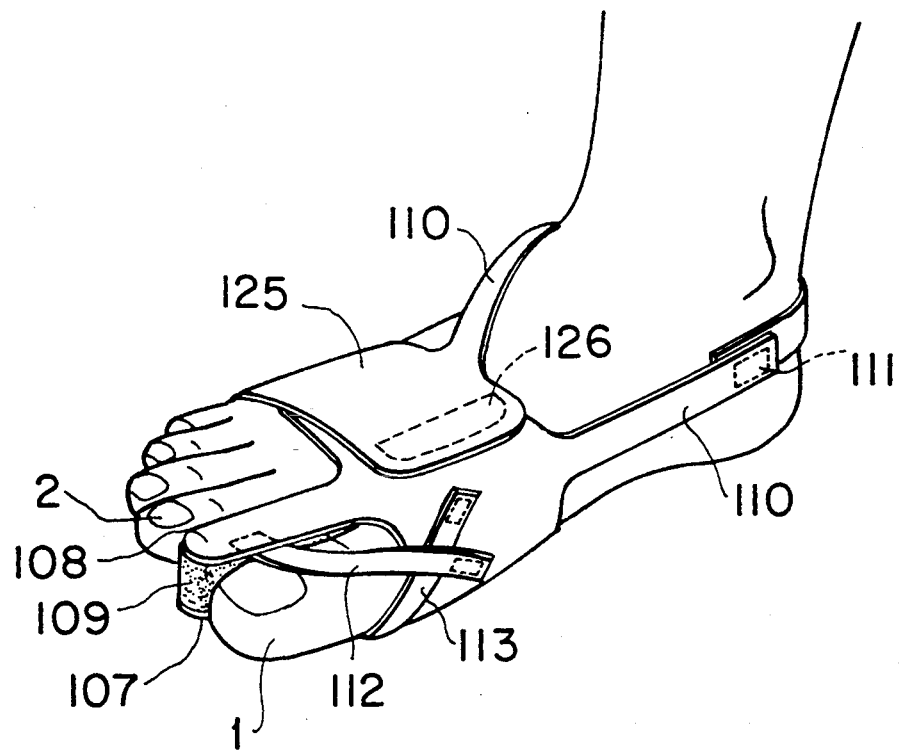
FIG. 24 is a perspective view of the twelfth embodiment of the present invention which shows the state in use.

FIGS. 23 and 24 show a twelfth embodiment of the present invention. The twelfth embodiment is similar to the eleventh embodiment, except that the position of the hook and loop fastener 126 of a metatarsophalangeal joint band 125 and the position of the hook and loop fastener 131 of the pulling band 130 are changed to the opposite sides. Since other structure and function are the same as those of the eleventh embodiment, the same parts are indicated with the same reference numerals and the description is omitted.

Figure 25:
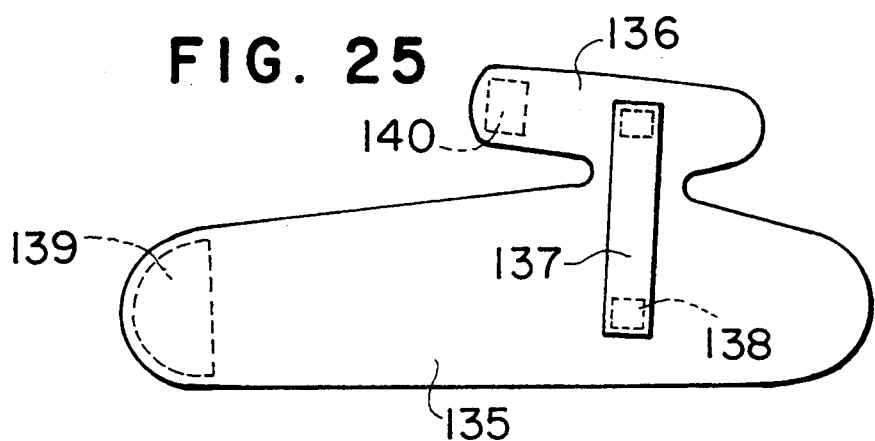
FIG. 25 is a front view of a thirteenth embodiment of the present invention.
Figure 26:
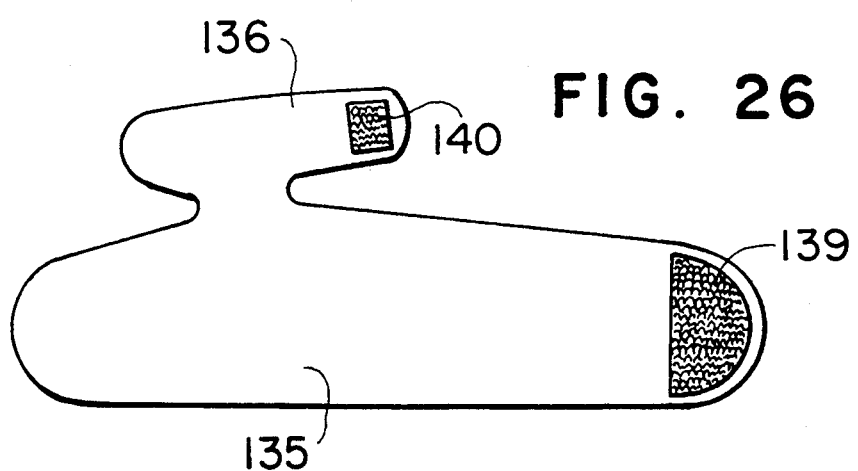
FIG. 26 is a bottom plan view of the thirteenth embodiment of the present invention.
Figure 27:
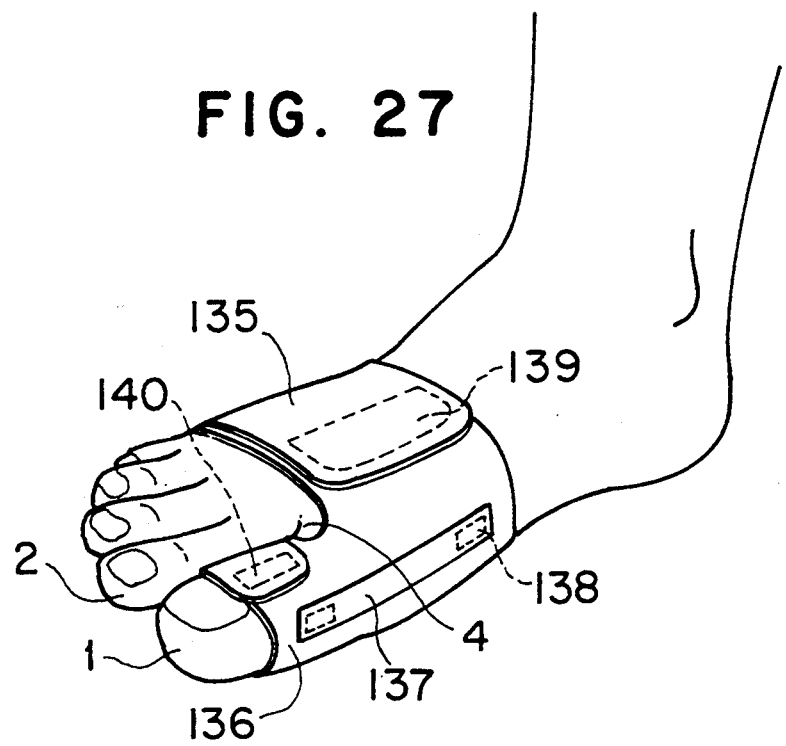
FIG. 27 is a perspective view of the thirteenth embodiment of the present invention which shows the state in use.
Figure 30:
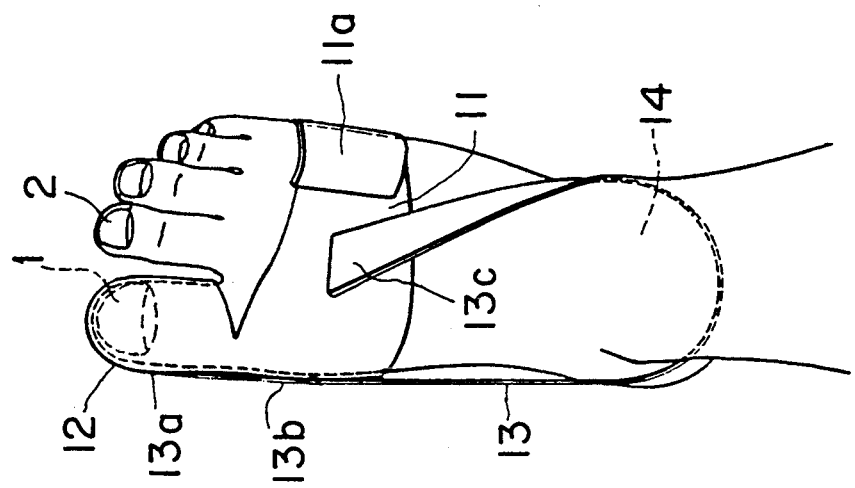
FIG. 30 is a plan view of the prior valgus big toe rectifying supporter which shows the state in use.
Figure 29:
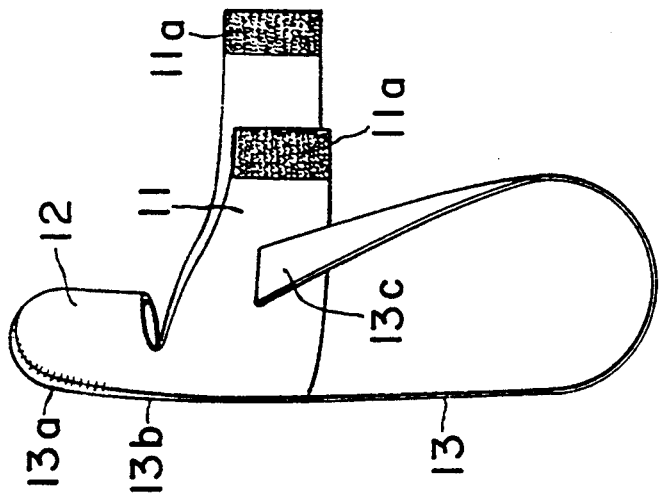
FIG. 29 is a plan view of a prior valgus big toe rectifying supporter.
Figure 28:
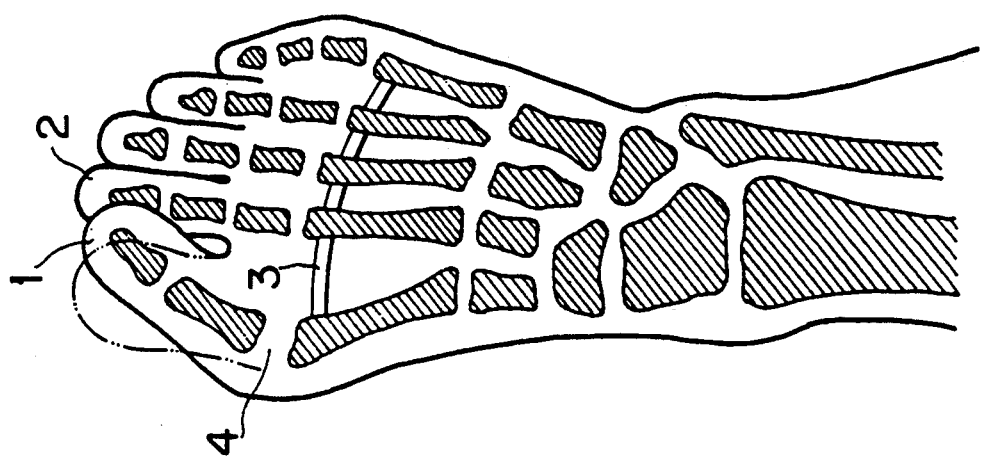
FIG. 28 is a view illustrating the skeleton of a valgus big toe.

FIGS. 25 and 27 show a thirteenth embodiment of the present invention. A metatarsophalangeal joint securing band 135 can be firmly wound laterally the metatarsophalangeal joint 4 at the root of the big toe so that the metatarsophalangeal joint 4 may be securely held. The big toe securing band 136 will be wound around the big toe. The lower intermediate section of the metatarsophalangeal joint securing band 135 and the upper intermediate section of the big toe securing band 136 are connected, a pulling band 137 is attached vertically on the connection section, the upper section of the pulling band 137 is fixed to the big toe securing band 136, and a hook and loop fastener 138 is attached to the inner surface of the lower end of the pulling band 137.

Hook and loop fasteners 139 and 140 are attached respectively to the undersurface of one end of the metatarsophalangeal joint securing band 135 and the undersurface of one end of the big toe securing band 136.

When it is put to use, as shown in FIG. 3, the metatarsophalangeal joint securing band 135 is wound firmly around the metatarsophalangeal joint 4 so that it may be kept in a fastened state by the hook and loop fastener 139. Then, the big toe securing band 136 is wound around the big toe 1 and it is kept in a fastened state by the hook and loop fastener 140. Then the pulling band 137 is pulled to pull the big toe 1 to its normal position to push the metatarsophalangeal joint 4 inwardly to its normal position, and the lower end of the pulling band 137 is fixed to the metatarsophalangeal joint securing band 135 to keep that state.

What is claimed is:

1. A valgus big toe rectifying supporter comprising a metatarsophalangeal joint securing band adapted to be wound around the metatarsophalangeal joint, said securing band having a top portion adapted to be disposed about the top of a person's foot and a bottom portion adapted to be disposed about the bottom of a person's foot, said top portion having a top front edge which includes a first top front edge section adapted to be disposed at the root of the big toe and a second top front edge section adapted to be juxtaposed to the roots of the second toe, the third toe, the fourth toe, and the little toe, said bottom portion of said securing band having a bottom front edge which includes a first bottom front edge section adapted to be disposed at the root of the big toe and a second bottom front edge section adapted to be juxtaposed to the roots of the second toe, the third toe, the fourth toe, and the little toe, said top portion of said securing band having a top forward projection projecting forwardly from said top front edge between said first and second top front edge sections, said top forward projection being adapted to generally overlie the space between the big toe and the second toe, said bottom portion of said securing band having a bottom forward projection projecting forwardly from said bottom front edge between said first and second bottom front edge sections, said bottom forward projection underlying said top forward projection, a resilient member jointed to said top forward projection and said bottom forward projection, said resilient member being adapted to be disposed and retained between the big toe and the second toe.

2. A valgus big toe rectifying supporter according to claim 1 wherein said securing band has an outer end section adapted to be disposed about the outer side of a person's foot and joined to said second top front edge section and to said second bottom front edge section, said second top front edge section and said second bottom front edge section along with said outer end section defining an opening space having a width substantially equal to the total width of the second toe, the third toe, the fourth toe and the little toe.

3. A valgus big toe rectifying supporter according to claim 1 wherein said top and bottom forward projections are integrally formed with said securing band as one piece.

4. A valgus big toe rectifying supporter according to claim 1 further comprising detachable fastening means for detachably fastening said top forward projection to said securing band.

5. A valgus big toe rectifying supporter according to claim 1 wherein said securing band is adapted to be completely wrapped around a person's foot, and detachable fastening means on said band operable to be attached and detached to enable said securing band to be wrapped and unwrapped around a person's foot.

6. A valgus big toe rectifying supporter according to claim 5 wherein said securing band comprises two detachable fastening means each circumferentially spaced from one another when the supporter is applied for use on a person;s foot.

7. A valgus big toe rectifying supporter according to claim 1 wherein said securing band is integrally formed as one piece to completely encircle a person's foot.

8. A valgus big toe rectifying supporter according to claim 1 further comprises a strap extending rearwardly of said securing band and adapted to encircle the heel of the person to which the supporter has been applied for use.

9. A valgus big toe rectifying supporter according to claim 1 further comprising a pulling band attached to said top forward projection, said pulling band extending laterally and rearwardly of said top forward projection, said pulling band having a rear end part overlying said securing band, and detachable attaching means detachably attaching said pulling band to said securing band.

10. A valgus big toe rectifying supporter according to claim 9 wherein said pulling band is designated a first pulling band, further comprising a second pulling band attached to said bottom forward projection, said pulling band extending laterally and rearwardly of said bottom forward projection, and detachable attaching means detachably attaching said second pulling band to said securing band.

11. A valgus big toe rectifying supporter according to claim 10 wherein said first and second pulling bands cross over one another.

* * * * *